United States Patent [19]

Rise

[11] 4,390,023

[45] Jun. 28, 1983

[54] PATTERNED ELECTRICAL TISSUE STIMULATOR

[75] Inventor: Mark T. Rise, Minneapolis, Minn.

[73] Assignee: Medtronic, Inc., Minneapolis, Minn.

[21] Appl. No.: 259,099

[22] Filed: Apr. 30, 1981

[51] Int. Cl.³ .............................................. A61N 1/32
[52] U.S. Cl. .................................................. 128/421
[58] Field of Search ............. 128/419 P, 419 F, 419 E, 128/419 G, 421, 422, 423, 795, 796, 1 B, 419 R; 364/413, 770

[56] References Cited

U.S. PATENT DOCUMENTS

| | | | |
|---|---|---|---|
| 2,864,371 | 12/1958 | Parodi | 128/419 R |
| 3,814,106 | 6/1974 | Berkovits | 128/421 |
| 3,902,502 | 9/1975 | Liss et al. | 128/422 |
| 4,066,086 | 1/1978 | Alferness et al. | 128/419 PG |
| 4,192,316 | 3/1980 | Walters et al. | 128/419 PG |
| 4,227,516 | 10/1980 | Meland et al. | |
| 4,237,899 | 12/1980 | Hagfors et al. | |
| 4,324,253 | 4/1982 | Greene et al. | 128/421 |

FOREIGN PATENT DOCUMENTS

10364  4/1980  European Pat. Off. .

OTHER PUBLICATIONS

"A Serial to Parallel Interface System for Tens Pain Suppression", Petrucelli et al.
"Conference on Cutaneous Communication Systems and Devices", Saunders, 1973.
"Electrical Stimulation of Pain and Touch", R. H. Gibson.
"Pain Control by Transcutaneous Electrical Nerve Stimulating Using Irregular Pulse of 1/f Fluctuation", Kintoma Takakura et al, Applied Neurophysiology, vol. 42, 1979, pp. 314–315.
"The Empi Tens System", Advertisement, Empi, Inc., 1981.
"Theoretical Design and Implementation of a Transcutaneous, Multichannel Stimulator For Neural Prosthesis Applications", Ian C. Forster, 3/80.
David I. Aidley, *The Physiology of Excitable Cells*, 2nd Edition Cambridge Univ. Press, ©1978, pp. 153–155.

*Primary Examiner*—William E. Kamm
*Assistant Examiner*—Mitchell J. Shein
*Attorney, Agent, or Firm*—Merchant, Gould, Smith, Edell, Welter & Schmidt

[57] ABSTRACT

A patterned electrical tissue stimulator includes a current source and analog multiplexers connected to an array of electrodes attached to the body. Microprocessor control of the multiplexer and the current source provides automatic selection of electrode stimulation pairs whereby spatial patterns of electrical stimulation are produced. Temporal summation and temporal patterns of electrical stimulus are provided through microprocessor control of the current source.

5 Claims, 6 Drawing Figures

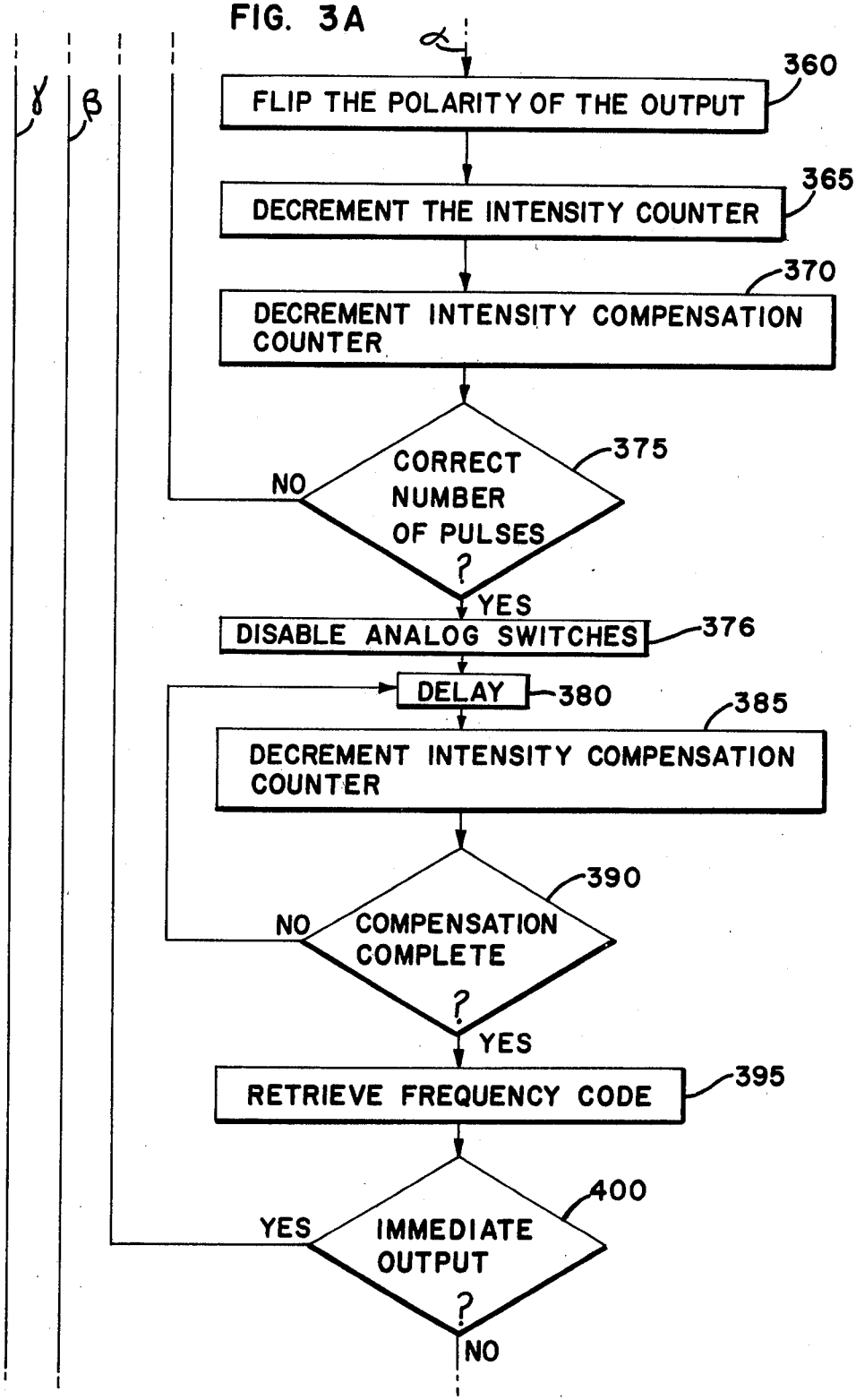

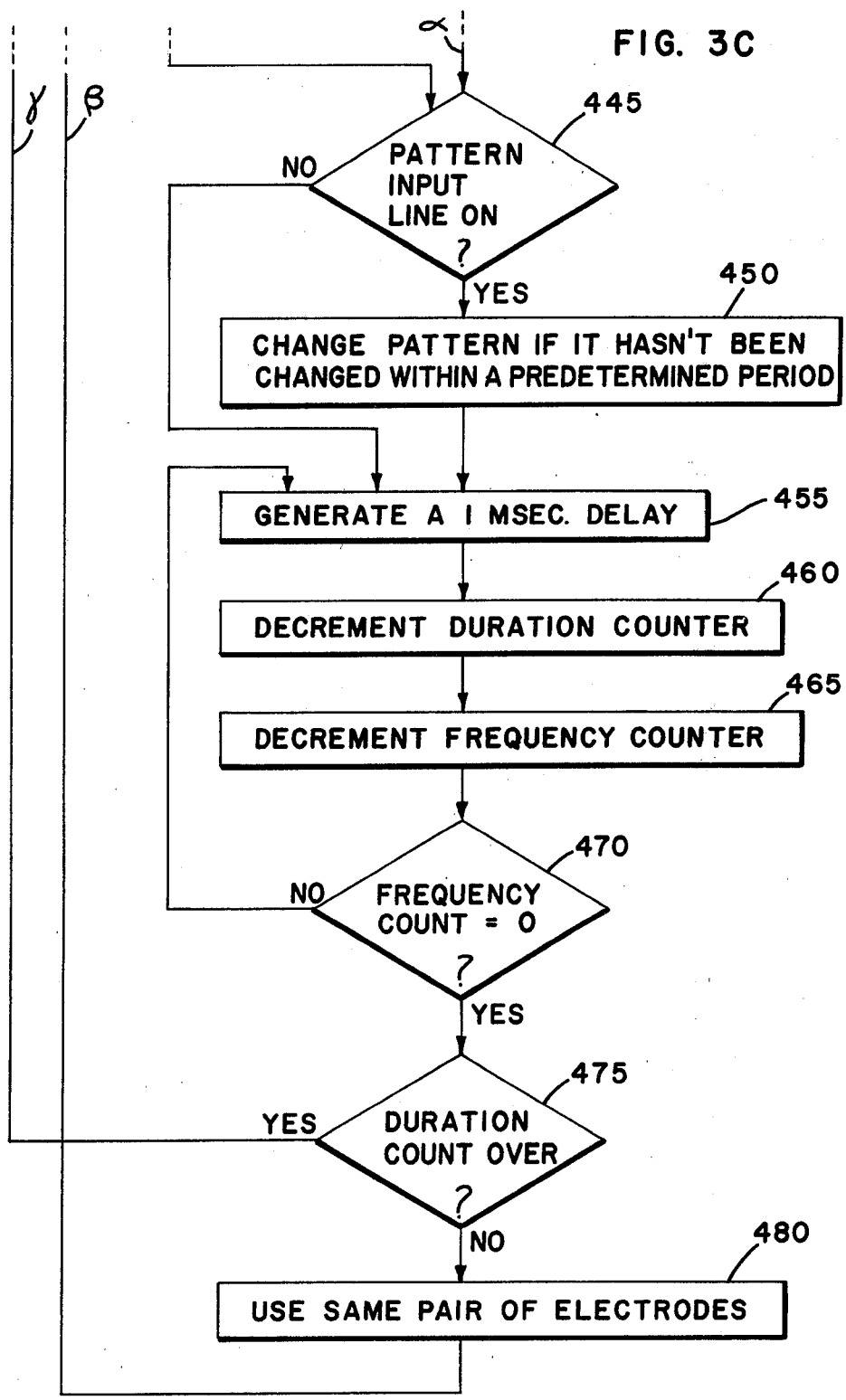

PATTERNED ELECTRICAL TISSUE STIMULATOR

TECHNICAL FIELD OF THE INVENTION

The invention pertains to the field of nerve stimulators used in the field of medicine for the relief of pain. More particularly, the invention relates to an automatically controlled electrical tissue stimulator for use with a multiple electrode system for generating spatially and temporally patterned electrical nerve stimulation.

BACKGROUND OF THE INVENTION

Electrical nerve stimulators have become widely used in recent years in the field of medicine for the treatment of chronic intractable pain. Such devices include circuitry for generating electrical pulses, and electrode leads for delivering the pulses to the site of pain within the body. The electrical stimulating pulses produce the effect of masking the sensation of pain, and this method is preferable to drug therapy for many types of pain, because it avoids subjecting the patient to possible dangerous side effects. In the control of chronic pain by a nerve stimulator, there are generally provided adjustments or controls so that the stimulation delivered by the device can be adjusted or controlled according to the needs of the patient, which sometimes vary from day to day, or even minute to minute. Ideally, the stimulus repetition rate, the stimulus intensity, and the stimulus situs should be controllable to provide maximum flexibility in meeting the patient's needs. Transcutaneous stimulators are worn or carried outside the body and have electrodes secured to the skin over the affected area to apply the electrical stimulation thereto. Generally, transcutaneous stimulators comprise a set of electrodes or an electrode pair with leads connected to a portable controller, with adjustments for stimulus frequency and intensity. Electrical stimulation is generally provided with pulses that may be adjusted for varying frequency, width, or amplitude. In the prior art, monophasic and bi-phasic type pulses are generally used.

Monophasic type pulses induce current in the body tissue that flows in only one direction, the electrodes having a fixed polarity. It is generally known in the art that monophasic pulses of this type produce a "stinging" sensation or pain for the patient. The bi-phasic pulse is comprised of two sequential monophasic pulses of alternating polarity. In this manner, electrical nerve stimulation may be produced without a net DC current, thus avoiding the "stinging" pain associated with it.

While the most common method of controlling stimulation intensity is varying the pulse width or amplitude, the technique of temporal integration or temporal summation is also known in the art. To achieve varying degrees of stimulation intensity using temporal summation, two or more threshold or sub-threshold stimulation pulses are delivered to the body tissue in a sufficiently short period of time so that they are summed or integrated to produce a discernible stimulus. Hereinafter these "pulse trains" will be referred to as pulse bursts. The technique is advantageous in that a series of relatively low amplitude pulses (approximately 5 milliamps or less) may be used to produce stimulation requiring 80 milliamps or more using the single pulse stimulation method. Specifically, the advantage comes from being able to use a standard FET current source as opposed to the fly back transformer or pulse transformer current source most commonly used in the single pulse method and from the reduced likelihood of the patient's experiencing "stinging pain".

In a conventional electrical nerve stimulation system, stimulation pulses are delivered to body tissue through one pair of electrodes. Generally, each electrode has an area on the order of 4.5 square inches. While this method is advantageous because of its simplicity, it is hindered by its poor ability to distribute current uniformly throughout the volume of tissue beneath and between electrode pads. The problem is generally attributed to the varying conductivity of the tissue and the tissueelectrode interface. Usually, local tissue breakdown results in a single isolated current path from one electrode to the other. Through the use of a multiple electrode system where each electrode has an area on the order of 10 square millimeters, this problem has been alleviated. However, to operate a multiple electrode system using the conventional single pulse method, it is necessary that each electrode pair have an independent current source. This is generally impractical in a portable system because of space and weight limitations. In addition to providing for better current distribution in the stimulated tissue, the multiple electrode system may be used to generate spatial patterns of stimulation. Such a prior art device exists, using switches to manually select spatially separated electrode pairs.

While pulse width and pulse amplitude provide control over perceived stimulus intensity, it is well known that controlling the pulse rate may also improve the efficacy of stimulation. Many prior art devices provide adjustable pulse rate with a manual control. While such manual control provides the patient with a means for varying the stimulus perception when any particular pulse rate becomes painful, annoying, or imperceptible, the method usually requires that the patient adjust the pulse rate regularly. This is sometimes impracticable, i.e., if the patient is sleeping or his hands are immobile. Much of the difficulty associated with manual adjustment of pulse rate has been overcome through the use of automatic controls that vary the pulse rate randomly or rhythmically, such as the 1/f fluctuation technique. Findings have shown that such methods are also more effective in alleviating pain. See Pain Control by Transcutaneous Electrical Nerve Stimulating Using Irregular Pulse of 1/f Fluctuation, Kintomo Takakura, Keiji Sano, Yukio Kosugi & Jyun Ikebe, Applied Neurophysiology, D. 42, 1979, page 314. The efficacy of electrical nerve stimulation is also improved by modulating the frequency of the pulse rate variation.

Although the automatic control of pulse rate, pulse width, and pulse amplitude has been provided for in prior art systems, an automatic system combining these features with spatial variation of the stimulus situs has not. However, due to the wide variety of patient needs, a demand exists for such a system.

SUMMARY OF THE INVENTION

The present invention is an apparatus and method for producing patterned electrical tissue stimulation comprising a current generation means connected through a multiplexing means to a plurality of electrodes, the multiplexing means and the current means being connected to a control means, whereby electrical tissue stimulation is produced.

BRIEF DESCRIPTION OF THE DRAWING

In the drawing:

FIGS. 3, 3a, 3b, and 3c are a flow chart of the software according to the present invention.

DETAILED DESCRIPTION OF THE PREFERRED EMBODIMENT

Figure 1:
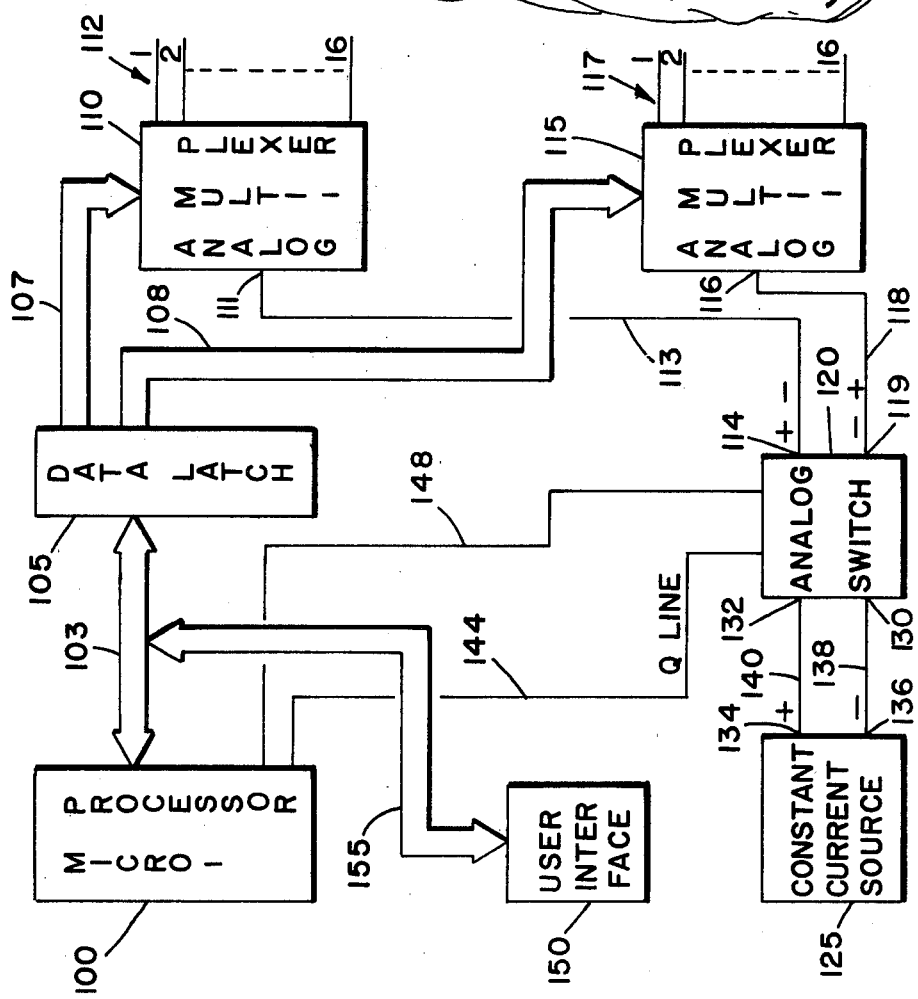
FIG. 1 is a block diagram of a Patterned Electrical Nerve Stimulator according to the present invention.

The invention as embodied in the block diagram of FIG. 1 comprises seven principal components: user interface 150, microprocessor 100, data latch 105, analog multiplexers 110 and 115, analog switch 120, and constant current source 125. In the embodiment, microcomputer 100 functions as the controller for elements 110, 115, and 120. While the embodiment shown in FIG. 1 utilizes an 1802 type microcomputer, any microcomputer or custom designed controller chip capable of performing the necessary functions may be substituted. User interface 150, which is connected to microprocessor 100 through multi-line connector 155, provides for on/off and stimulus intensity control.

Data latch 105 is connected to microcomputer 100 through data bus 103. It serves to store and synchronize output data from microcomputer 100 for control of analog multiplexers 110 and 115. Data buses 107 and 108 carry control data out of data latch 105 into analog multiplexers 110 and 115, respectively. Buses 107 and 108 each comprise four individual data lines which deliver multiplexing information to analog multiplexers 110 and 115.

Figure 2:
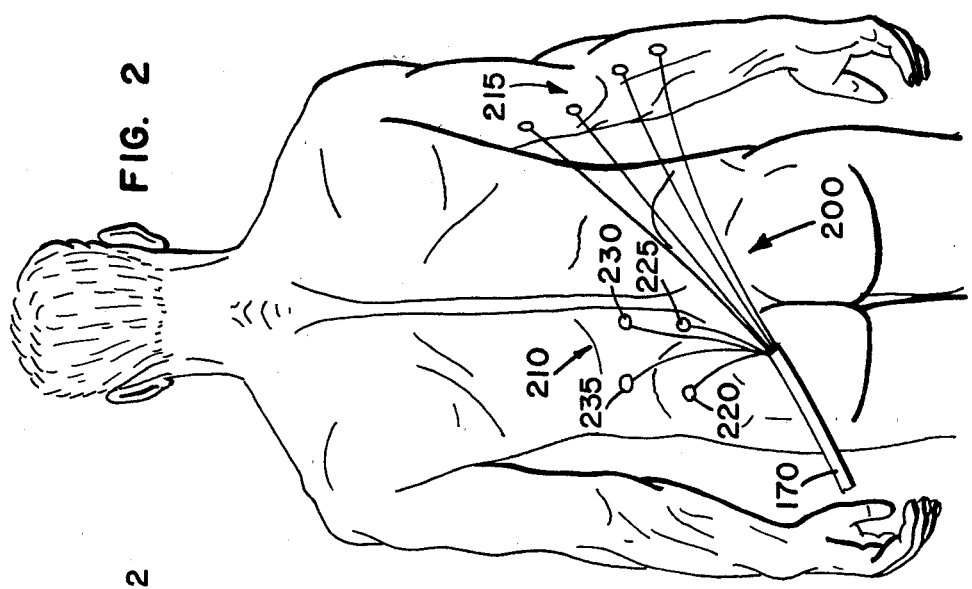
FIG. 2 is an illustration of possible electrode placement on a patient.

Analog multiplexers 110 and 115 provide for a 1 to 16 multiplex. The parallel four bit codes applied through data buses 107 and 108 to the multiplexers 110 and 115 respectively, determine the multiplexing connections. Output lines 112 and 117 are connected through a suitable conductor arrangement 170 so that either input lines 111 or 116 to the respective analog multiplexers 110 and 115 may be connected to any of the 16 electrodes 200 (only eight are depicted) as shown in FIG. 2. While the embodiment shown in FIG. 1 features a dual 1 to 16 multiplexing system, it will be seen that minor modifications would provide for a lesser or greater multiplexing capability.

The inputs to analog multiplexers 110 and 115 are connected through conductors 113 and 118 to the respective outputs 114 and 119 of analog switch 120. Microprocessor Q line output 144 controls analog switch 120 so that outputs 114 and 119 may be connected to inputs 132 and 130, respectively, or 130 and 132, respectively. On/off control of analog switch 120 is provided for by line 148 to microprocessor 100. Inputs 132 and 130 are connected through conductors 140 and 138 to respective outputs 134 and 136 of constant current source 125. As illustrated, outputs 134 and 136 of constant current source 125 have the respective polarities of positive and negative. In the described configuration it will be seen that the polarity of outputs 114 and 119 toggle or alternate in response to signals input from Q line 144 to analog switch 120.

In the preferred embodiment, electrode array 200 comprises 16 independent transcutaneous electrodes each with an area on the order of 10 square millimeters. However, it will be seen that electrode array 200 may be comprised of subcutaneous electrodes. The electrodes comprising array 200 may be of any type generally known in the art, only reduced in size. Each electrode in the array has two connections, one to a corresponding output 112 of multiplexer 110 and the other to the corresponding output 117 of multiplexer 115. For example, electrode 235 would be connected to analog multiplexers 110 and 115 at each respective "1" output. This allows for any two electrodes in array 200 to be selected as a stimulus pair. The electrodes comprising electrode array 200, as shown in FIG. 2, may be secured to (or in) the patient's body to form any desirable arrangement. For example, the electrodes may be arranged in groups of four (210) or in a line (215). In any event, it is generally known in the art that a minimum spacing of approximately one to two inches is necessary in order for the patient to perceive a spatial separation of stimulus origin.

It is also generally known in the art that patients are unable to temporally distinguish between stimulation pulses effectuated within about 4 milliseconds of each other. In the preferred embodiment, this physiological limitation allows a single perceptible stimulation pulse to be produced with a sequential pulsing of two or more electrode pairs. The operation of the circuitry shown in FIG. 1 to create such an effect will be described in the following paragraphs.

For the purpose of illustration, imagine that the tissue below the perimeter defined by electrodes 235, 220, 225, and 230 (as shown in FIG. 2) is sought to be electrically stimulated. As will be explained later (in the software discussion), this task may be performed in the system's "immediate" mode. The four electrodes (i.e., 235, 220, 225, and 230) may be paired to form up to six independent combinations. As stated above, stimulation pulses delivered to any of the six possible pairs within a 4 millisecond period will be temporally indistinguishable to the patient. Due to circuit and technique limitations in the particular embodiment shown as hereinafter described, a maximum of four pairs of electrodes may be pulsed within any given 4 millisecond period. For this example, assume the four electrode pairs 235 and 230, 220 and 225, 220 and 230, and 235 and 225 will be sequentially pulsed so as to blend the four pulse bursts into a single perceived stimulation event.

Referring to FIG. 1, it will be seen that the first step in accomplishing the desired stimulation is connecting constant current source 125 outputs 134 and 136 to the first pair of electrodes 235 and 230, respectively. To do so, microprocessor 100 loads the proper multiplexing data into data latch 105 through data bus 103. This multiplex code is then conducted to multiplexers 110 and 115 through data buses 107 and 108, respectively, resulting in the connection of electrodes 235 and 230 to inputs 111 and 116. In the preferred embodiment, this sequence of events takes about 50 microseconds. Once the electrode pair has been connected, electrical tissue stimulation is produced by constant current source 125 and analog switch 120. Constant current source 125 produces a constant current of up to 5 milliamps between its outputs 134 and 136 given any reactance less than 2.5 kilohms. After enabling analog switch 120 through line 148, microprocessor Q line output 144 is used to toggle analog switch 120 so that bi-phasic pulses with a current amplitude of approximately 2–4 milliamps and a period of approximately 80 microseconds are delivered to the selected electrode pair. Although each individual bi-phasic pulse is marginally perceptible, a series of two or more produce an easily discernible effect. In the present example, approximately ten such pulses could be sequentially delivered to the electrode pair 235 and 213, consuming a total time interval of approximately 800 microseconds. It should be seen that while the toggling of electrode polarities could be accomplished by reversing the multiplexing connections, the additional time required to do so as compared with toggling analog switch 120 with Q line 144 makes it less desirable. While Q line 144 may be toggled with only a few instructions in the microprocessor, the reversal of multiplexing connections requires additional instructions and the further delay of data latch 105.

After delivering up to ten bi-phasic pulses to the first selected electrode pair, microprocessor 100 automatically connects the next pair. It will be seen that the total elapsed time between the connection of the first electrode pair, the subsequent pulsing, and the connection to the second electrode pair will be no more than 1 millisecond. In this manner, four distinct stimuli (pulse bursts) may be used to produce what is perceived by the patient as a single stimulation event or pulse. This technique provides a major advantage over the conventional two electrode system in that it can greatly enhance tissue current distribution without altering the patient's stimulus perception.

Figure 3:
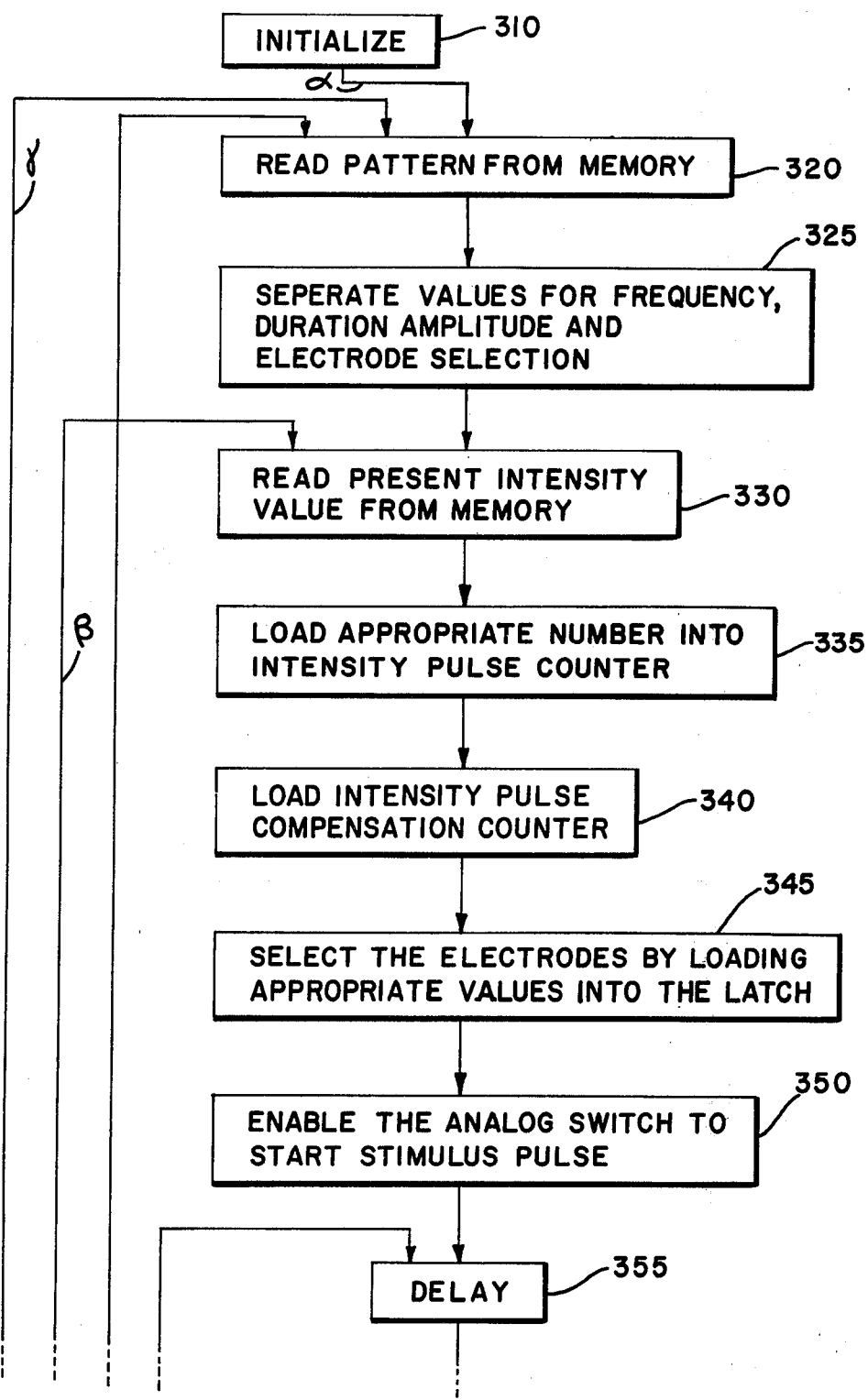
Figure 3B:
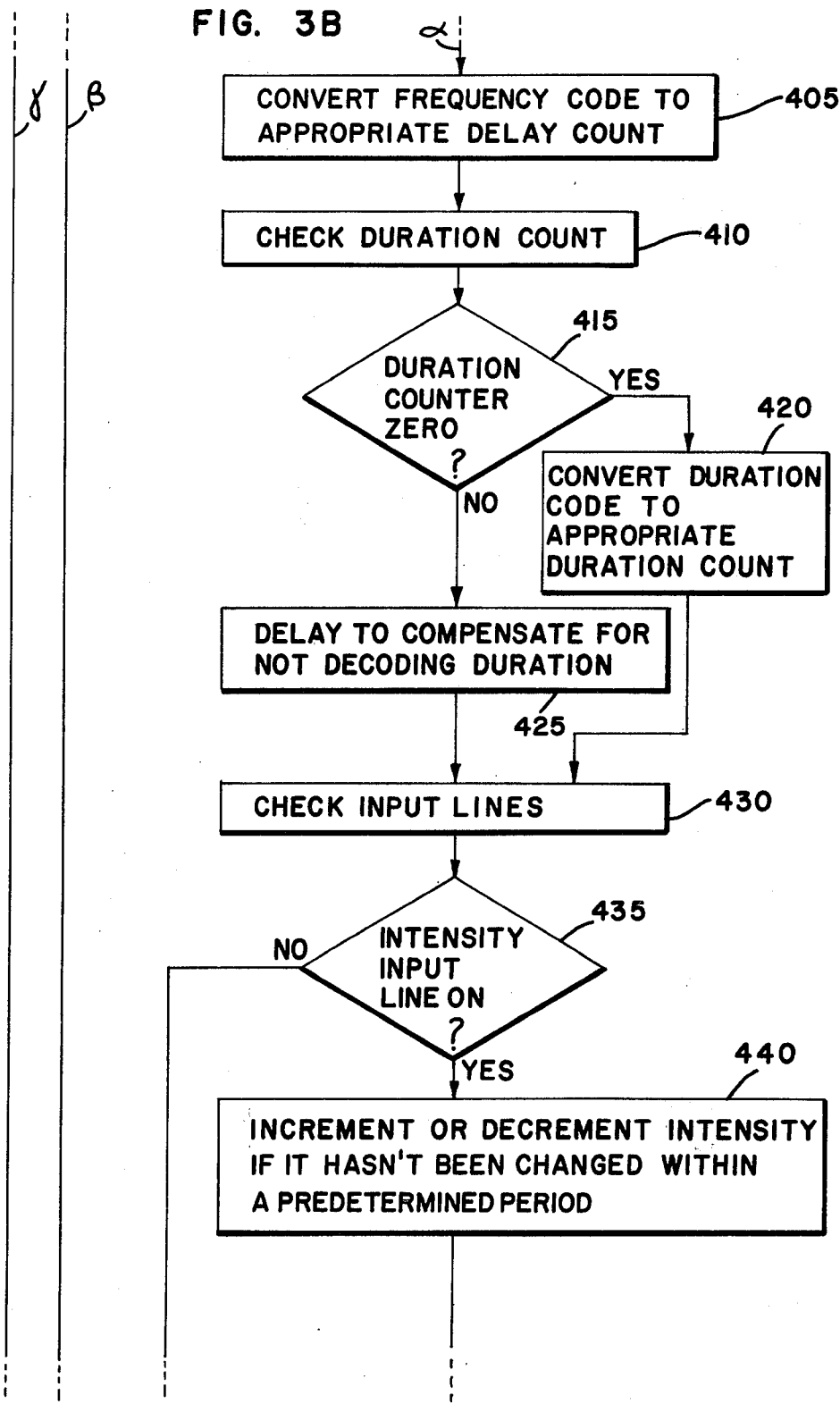

The microprocessor software most pertinent to the key operations of the present invention is flowcharted in FIG. 3. Initialize block 310 represents the functions performed by the microprocessor at the outset of each use. Initialize functions include, but are not limited to, such things as clearing data latches and presetting program counters. Flow chart box 320 represents the software code which retrieves stimulation instructions from memory chips such as EPROMS or ROMS. In the present embodiment these instructions are stored in two eight-bit words, one word containing the electrode pair choice and the other word frequency-duratin code. The frequency code controls the time between stimulation bursts (stimulation frequency), while the duration code controls the length of time between changes in the stimulation frequency. The stimulation frequency and its duration are both programmable. The former from 2 to 500 Hz and the latter from 500 milliseconds to 10 seconds. The software which decodes these eight-bit words into usable form is represented by box 325. Using a standard 4k ROM, it will be seen that up to 10 hours of continuously varying stimulation can be accomplished.

As previously described, user interface 150 includes two buttons for control of stimulus intensity. During the initialization process, microprocessor 100 presets the intensity control value to its minimum setting. Flow chart block 330 corresponds to the software which retrieves this intensity value from memory for use during the stimulation process. In the present embodiment, the intensity value controls the quantity of sequential bi-phasic pulses delivered during each pulse burst. Block 335 represents the software which places the intensity value retrieved from the memory into an intensity pulse counter. The compliment of this value is then loaded into the intensity pulse compensation counter (block 340). After these counters have been loaded, data latch 105 is loaded with the eight bits corresponding to the two selected electrodes (block 345). The software (indicated by block 350) then initiates the electrical nerve stimulation process by enabling analog switch 120.

Flow chart boxes 355-390 represent the software which produces bursts of bi-phasic pulses and the corresponding delays thereafter. Basically, a series of bi-phasic pulses is produced and then followed by a complementary delay period so as to maintain a uniform operational delay for all possible stimulation intensity levels. After each such burst is complete, the decoded frequency (decoded in box 325) is retrieved from the memory and analyzed by the software corresponding to box 400. This analysis reveals either a programmed delay or an "immediate" mode command. The "immediate" mode "if" statement in box 400 provides the means whereby the system can switch immediately to another electrode pair without a delay (e.g., as described in the illustrative example). If in the "immediate" mode the software relating to block 400 directs the microprocessor 100 to block 320, where the next segment of stimulation data is read from the memory.

When not in the "immediate" mode, the program advances to flow chart block 405, where the software represented thereby converts the frequency to an appropriate delay count. The software corresponding to block 410 interrogates the duration counter for decision in block 415. If the duration counter is equal to zero the program advances to block 420 where the duration code is converted to appropriate duration count. If the duration counter is not at zero, the program advances to software block 425, which comprises a software delay designed to simulate the delay introduced by block 420. From both blocks 420 and 425 the program advances to the software represented by blocks 430 through 450. The software represented by these blocks comprises the microprocessor 100 user interface 150 interrogation routine. This routine involves sensing the stimulation buttons on user interface 150. If either the increment or decrement button is currently depressed, the software will adjust the intensity value accordingly providing there have been no changes within the last three seconds (block 440). If neither button is depressed, the program will jump from block 430 to block 445. Program flow chart boxes 445 allow the pattern source to be altered during operation. For example, a patient may have several alternative patterns to choose from. These patterns may be in one master ROM or several smaller ones. Next, the program begins to loop through blocks 455 to 470. This routine provides for the delay from each stimulation burst to the next and for control of the duration of the stimulation frequency In the case where the duration period is incomplete, box 475 directs the program flow back to box 330 to reinitiate the process which begins therefrom. If the duration count is complete, box 475 directs the program flow to box 320 where new instructions are read from the memory and the stimulation process is reinitiated. While the foregoing program flow chart description describes in adequate detail the interaction and operation of the software of the present invention, it will be observed that other programs which adequately perform these and other tasks may be substituted.

It is readily seen that spatially modulated or patterned stimulation can be accomplished by changing the stimulating electrode pair or pairs every so often as necessary to produce a traveling stimulus sensation to the patient. In a similar manner, the frequency of stimulation may be varied automatically (by varying the duration code) so as to provide any known type of temporal variations (e.g., 1/f, rhythmic, random, or progressive). These spatial and temporal patterns are easily programmed into the memory media directly (e.g., using a PROM burner) or through any higher level software systems adapted for such use.

In the present invention, the capability to spatially and temporally modulate the electrical stimulus provides the means to overcome the problems normally associated with electrical nerve stimulation. For example, the habituation effects caused by excessive stimulation to any particular tissue situs or that induced by monotony of stimulation frequency and intensity. Furthermore, the present invention provides the means for ready adaptation of electrical stimulus technique so that a wide variety of patient needs may be satisfied.

```
FILE: TENS1:MARK        HEWLETT-PACKARD: 1802 Assembler                    Thu, 30 Apr 1981, 12:06

LOCATION OBJECT CODE LINE     SOURCE LINE

1  "1802"
                         2  ;     THIS IS THE SOFTWARE FOR THE PATTERNED TISSUE STIMULATOR
                         3  ;     DEVELOPED AT MEDTRONIC,INC. BY MARK T. RISE
                         4
0001 F8 00               5  START      LDI       00H            ;INITIALIZE REGISTERS
0002 B2                  6             PHI       2
0003 B3                  7             PHI       3
0004 B4                  8             PHI       4
0005 B5                  9             PHI       5
0006 B6                 10             PHI       6
0007 B7                 11             PHI       7
0008 B8                 12             PHI       8
0009 B9                 13             PHI       9
000A BA                 14             PHI       10
000B AA                 15             PLO       10
000C A8                 16             PLO       8
000D BB                 17             PHI       11
000E AB                 18             PLO       11
000F BC                 19             PHI       12
0010 BD                 20             PHI       13
0011 BE                 21             PHI       14
0012 AE                 22             PLO       14
0013 7A                 23             REQ
0014 F8 03              24             LDI       03
0016 A2                 25             PLO       2
                        26
0017 F8 01              27             LDI       01H            ;POINT TO PATTERN
                        28                                      ;ROM
0019 B1                 29             PHI       1
001A F8 F0              30             LDI       0F0H
001C A1                 31             PLO       1
001D E1                 32             SEX       1
001E 72                 33             LDXA
001F AC                 34             PLO       12
0020 AD                 35             PLO       13
0021 E1                 36  AGAIN      SEX       1              ;R(1) POINTER FOR
                        37                                      ;PATTERN LOCATION
0022 1E                 38             INC       14             DEBUG INSTR
0023 8D                 39             GLO       13             CHK PATTERN POSIT
0024 3A 2E              40             BNZ       STILL          ION FOR RESTART
0026 8C                 41             GLO       12             RELOAD PAT POSIT
0027 AD                 42             PLO       13             COUNTER
0028 F8 01              43             LDI       01H            PATTERN BACK TO
002A B1                 44             PHI       1
002B F8 F1              45             LDI       0F1H
002D A1                 46             PLO       1              ZERO PATTERN LOC
```

FILE: TENS1:MARK   HEWLETT-PACKARD: 1802 Assembler

LOCATION OBJECT CODE   LINE    SOURCE LINE

| LOCATION | OBJECT CODE | LINE | LABEL | OP | OPERAND | COMMENT |
|---|---|---|---|---|---|---|
| 002E | F0 | 47 | STILL | LDX | | ;RETRIEVE FREQ DURATION |
| | | 48 | | | | ;CODE |
| 002F | FA 07 | 49 | | ANI | 07 | ;GET LOW ORDER BITS |
| 0031 | A7 | 50 | | PLO | 7 | ;STORE BITS |
| 0032 | 72 | 51 | | LDXA | | ;RETRIEVE & ADVANCE |
| 0033 | FA F8 | 52 | | ANI | 0F8H | ;GET HIGH ORDER BITS |
| 0035 | F6 | 53 | | SHR | | |
| 0036 | F6 | 54 | | SHR | | |
| 0037 | F6 | 55 | | SHR | | |
| 0038 | A5 | 56 | | PLO | 5 | ;STORE |
| 0039 | 2D | 57 | | DEC | 13 | COUNT PAT POSITION |
| 003A | 82 | 58 | DURAT | GLO | 2 | ;SET INTENSITY |
| 003B | A3 | 59 | | PLO | 3 | ;SCRATCH PAD |
| 003C | F8 0B | 60 | | LDI | 0BH | ;SET INTENSITY COMP |
| 003E | A4 | 61 | | PLO | 4 | ;SCRATCH PAD |
| 003F | E1 | 62 | | SEX | 1 | |
| 0040 | 61 | 63 | | OUT | 1 | ;OUTPUT POSITION CODE |
| 0041 | E0 | 64 | | SEX | 0 | ;IMMEDIATE OUTPUT |
| 0042 | 62 | 65 | | OUT | 2 | ;TURN ON SWITCHES |
| 0043 | C4 | 66 | | NOP | | |
| 0044 | 2F | 67 | | DEC | 15 | ;DELAY 8 USEC |
| | | 68 | | | | |
| 0045 | 23 | 69 | INTER | DEC | 3 | ;DECREASE INT COUNT |
| 0046 | 24 | 70 | | DEC | 4 | ;DECREASE INT COMP COUNT |
| 0047 | 2F | 71 | | DEC | 15 | ;DELAY AGAIN |
| 0048 | 7B | 72 | | SEQ | | |
| 0049 | 7A | 73 | | REQ | | ;CHANGE OUTPUT POLARITY |
| 004A | 2F | 74 | | DEC | 15 | ;DELAY SO MORE |
| 004B | 83 | 75 | | GLO | 3 | ;CHECK FOR END-OF-PULSE |
| 004C | 32 53 | 76 | | BZ | OFF | ;BRANCH IF IT IS |
| 004E | 2F | 77 | | DEC | 15 | ;ANOTHER DELAY |
| 004F | 7B | 78 | | SEQ | | ;FLIP POLARITY |
| 0050 | 7A | 79 | | REQ | | |
| 0051 | 30 45 | 80 | | BR | INTER | ;START ANEW |
| | | 81 | | | | |
| 0053 | E0 | 82 | OFF | SEX | 0 | ;SET FOR IMMED OUTPUT |
| 0054 | 62 | 83 | | OUT | 2 | ;TURN OFF SWITCHES |
| 0055 | C4 | 84 | | NOP | | |
| | | 85 | | | | |
| 0056 | C4 | 86 | COMP | NOP | | ;DELAY FOR 48 USEC |
| 0057 | C4 | 87 | | NOP | | |
| 0058 | C4 | 88 | | NOP | | |
| 0059 | C4 | 89 | | NOP | | |
| 005A | 2F | 90 | | DEC | 15 | |
| 005B | 24 | 91 | | DEC | 4 | |
| 005C | 84 | 92 | | GLO | 4 | |
| 005D | 3A 56 | 93 | | BNZ | COMP | |
| | | 94 | | | | |
| | | 95 | | | | |
| | | 96 | | | | |
| 005F | 85 | 97 | | GLO | 5 | CHK FOR IMMEDIATE |
| 0060 | 32 21 | 98 | | BZ | AGAIN | RETURN |
| | | 99 | | | | |

FILE: TENS1:MARK        HEWLETT-PACKARD: 1802 Assembler                Thu, 30 Apr 1981, 12:07

LOCATION OBJECT CODE LINE    SOURCE LINE

```
                    100
                    101
0062 FD 15          102             SDI     15H         ;SUBTRACT FREQ CODE
0064 33 D5          103             BDF     HIGH        ;BRANCH TO HIGH FREQ
0066 85             104             GLO     5           ;THIS WILL DECODE
0067 FF 15          105             SMI     15H         ;THE FREQ AND SET
0069 3A 70          106             BNZ     TWO         ;THE COUNTER
006B F8 19          107             LDI     19H         ;SET COUNT AT 25
006D A6             108             PLO     6
006E 30 D7          109             BR      CONT
                    110
0070 85             111 TWO         GLO     5
0071 FF 16          112             SMI     16H         ;CODE WORD (00010110)
0073 3A 7A          113             BNZ     THREE
0075 F8 1F          114             LDI     1FH         ;COUNT TO 31
0077 A6             115             PLO     6
0078 30 D7          116             BR      CONT
                    117
007A 85             118 THREE       GLO     5
007B FF 17          119             SMI     17H         ;CODE WORD (00010111)
007D 3A 84          120             BNZ     FOUR
007F F8 27          121             LDI     27H         ;COUNT AT 39
0081 A6             122             PLO     6
0082 30 D7          123             BR      CONT
                    124
0084 85             125 FOUR        GLO     5
0085 FF 18          126             SMI     18H         ;CODE WORD (00011000)
0087 3A 8E          127             BNZ     FIVE
0089 F8 31          128             LDI     31H         ;COUNT NOW AT 49
008B A6             129             PLO     6
008C 30 D7          130             BR      CONT
                    131
008E 85             132 FIVE        GLO     5
008F FF 19          133             SMI     19H         ;CODE WORD (00011001)
0091 3A 98          134             BNZ     SIX
0093 F8 3D          135             LDI     3DH         ;COUNT TO 61
0095 A6             136             PLO     6
0096 30 D7          137             BR      CONT
                    138
0098 85             139 SIX         GLO     5
0099 FF 1A          140             SMI     1AH         ;FREQ CODE (00011010)
009B 3A A2          141             BNZ     SEVEN
009D F8 4B          142             LDI     4BH         ;COUNT TO 75
009F A6             143             PLO     6
00A0 30 D7          144             BR      CONT
                    145
00A2 85             146 SEVEN       GLO     5
00A3 FF 1B          147             SMI     1BH         ;FREQ CODE (00011011)
00A5 3A AC          148             BNZ     EIGHT
00A7 F8 5B          149             LDI     5BH         ;COUNT AT 91
00A9 A6             150             PLO     6
00AA 30 D7          151             BR      CONT
                    152
```

FILE: TENS1:MARK     HEWLETT-PACKARD: 1802 Assembler

LOCATION OBJECT CODE LINE     SOURCE LINE

| LOCATION | OBJECT CODE | LINE | SOURCE LINE | | | |
|---|---|---|---|---|---|---|
| 00AC | 85 | 153 | EIGHT | GLO | 5 | |
| 00AD | FF 1C | 154 | | SMI | 1CH | ;FREQ CODE (00011100) |
| 00AF | 3A B6 | 155 | | BNZ | NINE | |
| 00B1 | F8 6D | 156 | | LDI | 6DH | ;COUNT TO 109 |
| 00B3 | A6 | 157 | | PLO | 6 | |
| 00B4 | 30 D7 | 158 | | BR | CONT | |
| | | 159 | | | | |
| 00B6 | 85 | 160 | NINE | GLO | 5 | |
| 00B7 | FF 1D | 161 | | SMI | 1DH | ;FREQ CODE (00011101) |
| 00B9 | 3A C0 | 162 | | BNZ | TEN | |
| 00BB | F8 81 | 163 | | LDI | 81H | ;COUNT SET TO 129 |
| 00BD | A6 | 164 | | PLO | 6 | |
| 00BE | 30 D7 | 165 | | BR | CONT | |
| | | 166 | | | | |
| 00C0 | 85 | 167 | TEN | GLO | 5 | |
| 00C1 | FF 1E | 168 | | SMI | 1EH | ;FREQ CODE (00011110) |
| 00C3 | 3A CD | 169 | | BNZ | ELEVEN | |
| 00C5 | F8 2B | 170 | | LDI | 2BH | ;SET |
| 00C7 | A6 | 171 | | PLO | 6 | ;  COUNT |
| 00C8 | F8 01 | 172 | | LDI | 01H | ;      TO |
| 00CA | B6 | 173 | | PHI | 6 | ;         299 |
| 00CB | 30 D7 | 174 | | BR | CONT | |
| | | 175 | | | | |
| 00CD | F8 01 | 176 | ELEVEN | LDI | 01 | |
| 00CF | B6 | 177 | | PHI | 6 | |
| 00D0 | F8 8F | 178 | | LDI | 8FH | |
| 00D2 | A6 | 179 | | PLO | 6 | |
| 00D3 | 30 D7 | 180 | | BR | CONT | |
| | | 181 | | | | |
| 00D5 | 85 | 182 | HIGH | GLO | 5 | ;FOR HIGH FREQ, CODE IS |
| 00D6 | A6 | 183 | | PLO | 6 | ;SAME NO. AS DELAY COUNT |
| | | 184 | | | | |
| 00D7 | 98 | 185 | CONT | GHI | 8 | ;CHECK HIGH ORDER BITS |
| 00D8 | 3A DD | 186 | | BNZ | NZERO | ;FOR 0 - IF NOT, GO TO |
| | | 187 | | | | ;NZERO |
| 00DA | 88 | 188 | | GLO | 8 | ;CHECK LOW BITS FOR 0 |
| 00DB | 32 E7 | 189 | | BZ | CTON | ;IF ZERO GO TO CTON |
| | | 190 | | | | |
| 00DD | F8 00 | 191 | NZERO | LDI | 00 | ; LOAD # TO COMPENSATE |
| 00DF | B9 | 192 | | PHI | 9 | ;FOR NOT GOING THROUGH |
| 00E0 | F8 09 | 193 | | LDI | 09 | ;DECISION TREE |
| 00E2 | A9 | 194 | | PLO | 9 | |
| 00E3 | 28 | 195 | | DEC | 8 | ;COUNT 1 MSEC FOR DURAT |
| 00E4 | C0 017A | 196 | | LBR | PROC | |
| | | 197 | | | | |
| 00E7 | 87 | 198 | CTON | GLO | 7 | ;CHECK DURATION CODE WORD |
| 00E8 | 3A F9 | 199 | | BNZ | D1 | ;NOT ZERO CONTINUE |
| 00EA | F8 01 | 200 | | LDI | 01 | ;LOAD # INTO DURATION |
| 00EC | B8 | 201 | | PHI | 8 | ;COUNTER |
| 00ED | F8 F6 | 202 | | LDI | 0F6H | |
| 00EF | A8 | 203 | | PLO | 8 | |
| 00F1 | F8 00 | 204 | | LDI | 00H | COMPENSATE FOR TIME |
| 00F2 | B9 | 205 | | PHI | 9 | |

FILE: TENS1:MARK    HEWLETT-PACKARD: 1802 Assembler    Thu, 30 Apr 1981, 12:08

LOCATION OBJECT CODE LINE    SOURCE LINE

| Location | Object Code | Line | | Source Line | | Comment |
|---|---|---|---|---|---|---|
| 00F3 | F8 08 | 206 | | LDI | 08H | |
| 00F5 | A9 | 207 | | PLO | 9 | |
| 00F6 | C0 017A | 208 | | LBR | PROC | |
| | | 209 | | | | |
| 00F9 | FF 01 | 210 | D1 | SMI | 01 | SET COUNT TO 1000 |
| 00FB | CA 010D | 211 | | LBNZ | D2 | FOR 1 SEC DURATION |
| 00FE | F8 03 | 212 | | LDI | 03 | |
| 0100 | B8 | 213 | | PHI | 8 | |
| 0101 | F8 E8 | 214 | | LDI | 0E8H | |
| 0103 | A8 | 215 | | PLO | 8 | |
| 0104 | F8 00 | 216 | | LDI | 00H | COMPENSATE FOR TIME |
| 0106 | B9 | 217 | | PHI | 9 | |
| 0107 | F8 07 | 218 | | LDI | 07H | |
| 0109 | A9 | 219 | | PLO | 9 | |
| 010A | C0 017A | 220 | | LBR | PROC | |
| | | 221 | | | | |
| 010D | 87 | 222 | D2 | GLO | 7 | |
| 010E | FF 02 | 223 | | SMI | 02 | |
| 0110 | 3A 21 | 224 | | BNZ | D3 | ;SET COUNT TO 1500 |
| 0112 | F8 05 | 225 | | LDI | 05 | FOR 1.5 SEC DURAT |
| 0114 | B8 | 226 | | PHI | 8 | |
| 0115 | F8 DC | 227 | | LDI | 0DCH | |
| 0117 | A8 | 228 | | PLO | 8 | |
| 0118 | F8 00 | 229 | | LDI | 00H | COMPENSATE FOR TIME |
| 011A | B9 | 230 | | PHI | 9 | |
| 011B | F8 06 | 231 | | LDI | 06H | |
| 011D | A9 | 232 | | PLO | 9 | |
| 011E | C0 017A | 233 | | LBR | PROC | |
| | | 234 | | | | |
| 0121 | 87 | 235 | D3 | GLO | 7 | |
| 0122 | FF 03 | 236 | | SMI | 03 | |
| 0124 | 3A 35 | 237 | | BNZ | D4 | ;SET COUNT TO 2000 |
| 0126 | F8 07 | 238 | | LDI | 07 | FOR 2 SEC DURATION |
| 0128 | B8 | 239 | | PHI | 8 | |
| 0129 | F8 D0 | 240 | | LDI | 0D0H | |
| 012B | A8 | 241 | | PLO | 8 | |
| 012C | F8 00 | 242 | | LDI | 0 | |
| 012E | B9 | 243 | | PHI | 9 | |
| 012F | F8 05 | 244 | | LDI | 5 | |
| 0131 | A9 | 245 | | PLO | 9 | |
| 0132 | C0 017A | 246 | | LBR | PROC | |
| | | 247 | | | | |
| 0135 | 87 | 248 | D4 | GLO | 7 | |
| 0136 | FF 04 | 249 | | SMI | 04 | |
| 0138 | 3A 48 | 250 | | BNZ | D5 | |
| 013A | F8 0B | 251 | | LDI | 0BH | ;SET COUNT TO 2816 |
| 013C | B8 | 252 | | PHI | 8 | |
| 013D | F8 B8 | 253 | | LDI | 0B8H | |
| 013F | A8 | 254 | | PLO | 8 | |
| 0140 | F8 00 | 255 | | LDI | 0 | |
| 0142 | B9 | 256 | | PHI | 9 | |
| 0143 | F8 04 | 257 | | LDI | 4 | |
| 0145 | A9 | 258 | | PLO | 9 | |

FILE: TENS1:MARK     HEWLETT-PACKARD: 1802 Assembler             Thu, 30 Apr 1981, 12:08

LOCATION OBJECT CODE LINE     SOURCE LINE

```
0146 30 7A      259            BR      PROC
                260
0148 87         261 D5         GLO     7
0149 FF 05      262            SMI     05
014B 3A 5B      263            BNZ     D6
014D F8 0D      264            LDI     0DH          ;SET COUNT TO 4000
014F B8         265            PHI     8
0150 F8 A0      266            LDI     0A0H
0152 A8         267            PLO     8
0153 F8 00      268            LDI     0
0155 B9         269            PHI     9
0156 F8 03      270            LDI     3
0158 A9         271            PLO     9
0159 30 7A      272            BR      PROC
                273
015B 87         274 D6         GLO     7
015C FF 06      275            SMI     06
015E 3A 6E      276            BNZ     D7
0160 F8 13      277            LDI     13H          ;SET COUNT TO 5000
0162 B8         278            PHI     8
0163 F8 88      279            LDI     88H
0165 A8         280            PLO     8
0166 F8 00      281            LDI     0
0168 B9         282            PHI     9
0169 F8 02      283            LDI     2
016B A9         284            PLO     9
016C 30 7A      285            BR      PROC
                286
016E F8 27      287 D7         LDI     27H          ;SET COUNT TO 10000
0170 B8         288            PHI     8
0171 F8 10      289            LDI     10H
0173 A8         290            PLO     8
0174 F8 00      291            LDI     0
0176 B9         292            PHI     9
0177 F8 01      293            LDI     1
0179 A9         294            PLO     9
                295
017A C4         296 PROC       NOP                  ;DELAY LOOP TO ADJUST
017B C4         297            NOP                  ;TIMING OF DECISION
017C C4         298            NOP                  ;TREE TO BE CONSTANT
017D C4         299            NOP
017E 29         300            DEC     9
017F 89         301            GLO     9
0181 3A 7A      302            BNZ     PROC
0182 30 BD      303            BR      INPUT
                304
0184 F8 08      305 INRET      LDI     08
0186 A9         306            PLO     9
0187 F8 00      307            LDI     00
0189 B9         308            PHI     9
                309
018A C4         310 FILL       NOP                  ;LOOP SO DECISION TREE
018B C4         311            NOP                  ;WILL BE 1MSEC
```

FILE: TENS1:MARK    HEWLETT-PACKARD: 1802 Assembler         Thu, 30 Apr 1981, 12:09

LOCATION OBJECT CODE LINE    SOURCE LINE

| | | | | |
|---|---|---|---|---|
| 018C 29 | 312 | DEC | 9 | |
| 018D 89 | 313 | GLO | 9 | |
| 018E 3A 8A | 314 | BNZ | FILL | |
| | 315 | | | |
| 0191 F8 00 | 316 FREQ | LDI | 00 | |
| 0192 B9 | 317 | PHI | 9 | |
| 0193 2A | 318 | DEC | 10 | CNT, IN DELAY |
| 0194 F8 15 | 319 | LDI | 15H | |
| 0196 A9 | 320 | PLO | 9 | |
| | 321 | | | |
| 0197 C4 | 322 DELAY | NOP | | 1 MSEC DELAY FOR |
| 0198 C4 | 323 | NOP | | FREQ |
| 0199 29 | 324 | DEC | 9 | |
| 019A 89 | 325 | GLO | 9 | |
| 019B 3A 97 | 326 | BNZ | DELAY | |
| 019D 26 | 327 | DEC | 6 | COUNT FOR FREQ |
| 019E 28 | 328 | DEC | 8 | COUNT FOR DURATION |
| 019F 98 | 329 | GHI | 8 | CHK FOR ROLLOVER |
| 01A1 FE | 330 | SHL | | OF REGISTER 8 |
| 01A1 3B AC | 331 | BNF | NOT | |
| 01A3 F8 00 | 332 | LDI | 00H | IF DURAT CNTER ROLLS |
| 01A5 A6 | 333 | PLO | 6 | OVER THEN RESET CNTRS |
| 01A6 A8 | 334 | PLO | 8 | TO ZERO |
| 01A7 B6 | 335 | PHI | 6 | |
| 01A8 B8 | 336 | PHI | 8 | |
| 01A9 C0 0021 | 337 | LBR | AGAIN | |
| 01AC 96 | 338 NOT | GHI | 6 | |
| 01AD 3A 90 | 339 | BNZ | FREQ | |
| 01AF 86 | 340 | GLO | 6 | |
| 01B0 3A 90 | 341 | BNZ | FREQ | |
| 01B2 98 | 342 | GHI | 8 | |
| 01B3 3A B9 | 343 | BNZ | OVER | |
| 01B5 88 | 344 | GLO | 8 | |
| 01B6 C2 0021 | 345 | LBZ | AGAIN | NEXT PAT POSIT |
| 01B9 21 | 346 OVER | DEC | 1 | SELECT SAME TRODES |
| 01BA C0 103A | 347 | LBR | DURAT | FOR OUTPUT AGAIN |
| 01BD 36 EA | 348 INPUT | B3 | NEWPAT | PATTERN INPUT "ON"? |
| | 349 | | | |
| 01BF 8B | 350 | GLO | 11 | 1ST TIME BY |
| 01C0 32 CB | 351 | BZ | NEW | |
| 01C2 9A | 352 | GHI | 10 | IF NOT THEN CHK IF |
| 01C3 FE | 353 | SHL | | DELAY CNTR HAS ROLLED |
| 01C4 3B 84 | 354 | BNF | INRET | GO BACK IF NOT |
| 01C6 F8 00 | 355 | LDI | 00H | IF SO, RESET 11 TO |
| 01C8 AB | 356 | PLO | 11 | PERMIT INPUT AND GO |
| 01C9 30 84 | 357 | BR | INRET | BACK TO PROGRAM |
| 01CB 34 D1 | 358 NEW | B1 | INC | CHK INCREASE BUTTON |
| 01CD 35 D9 | 359 | B2 | DEC | CHK DECREASE BUTTON |
| 01CF 30 84 | 360 | BR | INRET | NO INPUT;GO BACK |
| 01D1 82 | 361 INC | GLO | 2 | CHK FOR MAX INTENSITY |
| 01D2 FF 0A | 362 | SMI | 0AH | WHICH IS 10 PULSES |
| 01D4 32 84 | 363 | BZ | INRET | ALREADY AT MAX |
| 01D6 12 | 364 | INC | 2 | ;NOT AT MAX SO INCREASE |

```
01D7 30 DF        365           BR        COM         ;JUMP OVER DECREASE
01D9 82           366   DEC     GLO       2           ;CHK FOR MIN INTENSITY
01DA FF 01        367           SMI       01          WHICH IS ONE PULSE
01DC 32 84        368           BZ        INRET       ;ALREADY AT MINIMUM
01DE 22           369           DEC       2           ;DECREASE OUTPUT
01DF F8 FF        370   COM     LDI       0FFH        ;SET DELAY CONDITION
01E1 AB           371           PLO       11          TO PREVENT A RAPID
01E2 F8 13        372           LDI       13H         INCREASE OR DECREASE
01E4 BA           373           PHI       10          IN THE OUTPUT INTENSITY
01E5 F8 88        374           LDI       88H
01E7 AA           375           PLO       10
01E8 30 84        376           BR        INRET       RETURN TO PROGRAM
01EA C4           377   NEWPAT  NOP
                  378   ;NEWPAT........THIS IS THE PART OF THE PROGRAM THAT WILL CHECK TO
                  379   ;             DETERMINE WHETHER THE USER WANTS TO CHANGE THE PRESENT
                  380   ;             STIMULATION PATTERN. IF THE SWITCH IS ON, THE PROGRAM
                  381   ;             WILL CHANGE THE VALUE IN THE PATTERN LOCATION POINTER
                  382   ;             SO THAT A PATTERN STORED AT A DIFFERENT LOCATION IN
                  383   ;             MEMORY IS USED TO GENERATE THE STIMULUS OUTPUT. BY
                  384   ;             CONTINUING TO ACTIVATE THE PATTERN SWITCH, THE USER
                  385   ;             CAN TOGGLE THROUGH THE VARIOUS PATTERNS UNTIL HE FINDS
                  386   ;             THE ONE HE WANTS. THIS SUBROUTINE RETURNS TO THE
                  387   ;             PROGRAM AT "INRET".
01EB 30 84        388           BR        INRET

Errors=  0
```

What is claimed:

1. A portable automatically controlled electrical tissue stimulator comprising:
   means for producing electrical stimulation current, the polarity of said current controllable by a current control signal;
   a plurality of electrodes for attachment in an array to a patient to be treated;
   multiplexing means operatively connected between said current means and said electrodes, and responsive to a multiplexing signal for selectively connecting any pair of electrodes to said current means; and
   presettable automatic control means including memory means for storing presettable digitally encoded information indicative of a desired sequence of electrode pair connections and a desired number of current pulses to be applied to each of the pairs connected in the sequence and further including means responsive to said information stored in said memory means to produce said multiplexing signal and said current control signal to cause said electrodes to be sequentially connected to said current means automatically and stimulation current pulses of alternating polarity to be delivered to said pairs of said electrodes automatically.

2. An apparatus according to claim 2 wherein said presettable automatic control means comprises a microprocessor.

3. An apparatus according to claim 1, wherein said presettable automatic control means includes means for causing a plurality of electrode pairs to be connected in sequence to said means for producing electrical stimulation current, within a 4 msec period, so that the electrical stimulation delivered to each of said electrode pairs is temporarily indistinguishable to the patient.

4. An apparatus according to claim 1, wherein each of the current pulses produced by said means for producing said stimulation current are generated at an intensity level substantially equal to or less than the level of human perception.

5. An apparatus according to claim 4, wherein said presettable automatic control means includes means for causing a plurality of said current pulses to be delivered to a connected electrode pair within a duration of time short enough to cause said pulses to be temporarily summed in the stimulated tissue.

* * * * *

UNITED STATES PATENT AND TRADEMARK OFFICE
CERTIFICATE OF CORRECTION

PATENT NO. : 4,390,023
DATED : June 28, 1983
INVENTOR(S) : Mark T. Rise

It is certified that error appears in the above–identified patent and that said Letters Patent are hereby corrected as shown below:

Column 5,
    line 37, "frequency-duratin" should be --frequency-duration--;

Column 22,
    line 39, "claim 2" should be --claim 1--.

Signed and Sealed this

Seventeenth Day of July 1984

[SEAL]

*Attest:*

*Attesting Officer*

GERALD J. MOSSINGHOFF

*Commissioner of Patents and Trademarks*

UNITED STATES PATENT AND TRADEMARK OFFICE
CERTIFICATE OF CORRECTION

PATENT NO. : 4,390,023
DATED : June 28, 1983
INVENTOR(S) : Mark T. Rise

It is certified that error appears in the above-identified patent and that said Letters Patent is hereby corrected as shown below:

Column 2, line 13, "tissueelectrode" should be
--tissue-electrode--

Column 6, line 48, after "frequency" insert a period (.)

Claim 3, line 7, "temporarily" should be --temporally--

Claim 5, line 5, "temporarily" should be --temporally--

Signed and Sealed this

Nineteenth Day of March 1985

[SEAL]

Attest:

DONALD J. QUIGG

Attesting Officer    Acting Commissioner of Patents and Trademarks